United States Patent
Nagai

(10) Patent No.: US 10,416,077 B2
(45) Date of Patent: Sep. 17, 2019

(54) V-BLOCK REFRACTOMETER

(71) Applicant: Shimadzu Corporation, Kyoto (JP)

(72) Inventor: Tetsuya Nagai, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/075,793

(22) PCT Filed: Feb. 8, 2016

(86) PCT No.: PCT/JP2016/053707
§ 371 (c)(1),
(2) Date: Aug. 6, 2018

(87) PCT Pub. No.: WO2017/138083
PCT Pub. Date: Aug. 17, 2017

(65) Prior Publication Data
US 2019/0041327 A1    Feb. 7, 2019

(51) Int. Cl.
*G01N 21/41* (2006.01)
(52) U.S. Cl.
CPC .............. *G01N 21/4133* (2013.01)
(58) Field of Classification Search
CPC .. G01N 21/43; G01N 21/4133; G01N 21/431; A01N 37/16; A01N 59/00
USPC ........................................ 356/135
See application file for complete search history.

(56) References Cited

U.S. PATENT DOCUMENTS

| | | | | |
|---|---|---|---|---|
| 7,830,521 B2* | 11/2010 | Yamamoto | ........... | G01N 21/553 356/445 |
| 2008/0079951 A1* | 4/2008 | Yamamoto | ........... | G01N 21/553 356/600 |
| 2012/0092677 A1* | 4/2012 | Suehira | .................. | A61B 3/102 356/479 |
| 2016/0163077 A1 | 6/2016 | Sawayanagi | | |

FOREIGN PATENT DOCUMENTS

| | | |
|---|---|---|
| JP | H03-249508 A | 11/1991 |
| JP | H07-128228 A | 5/1995 |
| JP | 2006-98208 A | 4/2006 |
| WO | 2014/207809 A1 | 12/2014 |
| WO | 2015/001650 A1 | 1/2015 |

OTHER PUBLICATIONS

International Search Report dated Mar. 29, 2016 of corresponding International Application No. PCT/JP2016/053707; 5 pgs.

* cited by examiner

*Primary Examiner* — Md M Rahman
(74) *Attorney, Agent, or Firm* — Maier & Maier, PLLC

(57) ABSTRACT

A first data acquisition processing unit acquires light intensity distribution data on the basis of an image of measurement light that has entered a camera. A second data acquisition processing unit acquires light intensity distribution data on the basis of the detected intensity of measurement light detected by a detector. A refractive index measurement processing unit measures the refractive index of a sample on the basis of the light intensity distribution data acquired by the second data acquisition processing unit. A determination processing unit determines whether the refractive index of the sample measured by the refractive index measurement processing unit is acceptable on the basis of the peaks of the light intensity distribution data acquired by the first data acquisition processing unit and second data acquisition processing unit.

5 Claims, 5 Drawing Sheets

V-BLOCK REFRACTOMETER

FIELD

The present invention relates to a V-block refractometer that measures a refractive index of a sample by irradiating the sample with measurement light through a V-block prism.

BACKGROUND

In a V-block refractometer which is an example of a refractometer, a sample is placed in a V-shaped groove formed on a V-block prism, and the sample is irradiated with measurement light through the V-block prism. In this way, a refractive index of the sample may be measured by detecting measurement light penetrating the sample using a detector (for example, see Patent Document 1 below).

In this type of refractometer, a part of measurement light guided to the detector by penetrating the sample is separated by, for example, a beam splitter and guided to an eyepiece section (not illustrated). At the time of adjusting a position of the V-block prism, etc., an operator may perform an operation while visually observing a state of measurement light by looking into the apparatus from the eyepiece section.

However, in such a refractometer, the eyepiece section is covered with a cap during measurement to prevent light outside the apparatus from entering from the eyepiece section during measurement and influencing a detection result by the detector. For this reason, there is a problem that an actual state of measurement light may not be observed during measurement.

In this regard, there has been a considered configuration in which a camera is attached to the eyepiece section, incidence of light outside the apparatus from the eyepiece section is prevented, and measurement light is captured by the camera in the eyepiece section, thereby allowing observation of the image captured by the camera during measurement. Patent Document 2 below proposes a configuration in which a graph showing detected intensity of measurement light detected by a detector and an image of measurement light captured by a camera are displayed on one display screen in real time.

A refractive index of a sample is automatically calculated from a peak value of detected intensity of measurement light detected by a detector. However, for example, when the sample is a resin or a liquid, a refractive index of the sample becomes nonuniform in many cases. In such a case, when the refractometer to which the camera is attached is used, the operator may determine whether a state of the sample or a measurement result is acceptable by checking a shape of the graph and the image of the camera.

Patent Document 1: International Publication No. 2015/001650

Patent Document 2: International Publication No. 2014/207809

SUMMARY

However, when the operator checks the shape of the graph and the image of the camera, there is a problem that a determination result varies depending on the operator. In addition, such determination is not easy, and a skill is required to perform appropriate determination.

The invention has been made in view of above circumstances, and an object of the invention is to provide a V-block refractometer capable of easily and accurately determining whether a measured refractive index of a sample is acceptable.

(1) A V-block refractometer according to the invention is a V-block refractometer that measures a refractive index of a sample by irradiating the sample with measurement light through a V-block prism, the V-block refractometer including a light source unit, a slit, a camera, a detector, a first data acquisition processing unit, a second data acquisition processing unit, a refractive index measurement processing unit, and a determination processing unit. The light source unit irradiates measurement light. The measurement light irradiated from the light source unit passes through the slit. The measurement light passing through the slit is incident on the camera. The detector detects measurement light penetrating the sample. The first data acquisition processing unit acquires light intensity distribution data based on an image of the measurement light incident on the camera. The second data acquisition processing unit acquires light intensity distribution data based on detected intensity of the measurement light detected by the detector. The refractive index measurement processing unit measures the refractive index of the sample based on the light intensity distribution data acquired by the second data acquisition processing unit. The determination processing unit determines whether the refractive index of the sample measured by the refractive index measurement processing unit is acceptable based on each of peaks of the light intensity distribution data acquired by the first data acquisition processing unit and the second data acquisition processing unit.

According to such a configuration, it is determined whether a measured refractive index of a sample is acceptable based on the peak of the light intensity distribution data acquired based on the image of the measurement light incident on the camera and the peak of the light intensity distribution data acquired based on the detected intensity of the measurement light detected by the detector. In this way, it is possible to accurately determine whether a measured refractive index of a sample is acceptable using not only the detected intensity of the measurement light detected by the detector but also the image of the measurement light incident on the camera. In addition, it is possible to automatically and easily determine whether a measured refractive index of a sample is acceptable based on each the peak of the light intensity distribution data, and a determination result does not vary depending on the operator. Therefore, it is possible to easily and accurately determine whether a measured refractive index of a sample is acceptable.

(2) The refractometer may further include a width calculation processing unit that calculates a width corresponding to a range in which a ratio of light intensity to a peak value is a certain value or more with respect to a peak of light intensity distribution data acquired by at least one of the first data acquisition processing unit and the second data acquisition processing unit. In this case, the determination processing unit determines whether the refractive index of the sample measured by the refractive index measurement processing unit is acceptable based on the width calculated by the width calculation processing unit.

According to such a configuration, the width calculated with respect to the peak of the light intensity distribution data serves as an index as to whether the peak is steep. Thus, it is possible to accurately determine whether a measured refractive index of a sample is acceptable using such a width.

(3) The width corresponding to the range in which the ratio of the light intensity to the peak value is the certain value or more may be a full width at half maximum.

(4) The refractometer may further include an S/N ratio calculation processing unit that calculates an S/N ratio with respect to a peak of light intensity distribution data acquired by at least one of the first data acquisition processing unit and the second data acquisition processing unit. In this case, the determination processing unit determines whether the refractive index of the sample measured by the refractive index measurement processing unit is acceptable based on the S/N ratio calculated by the S/N ratio calculation processing unit.

According to such a configuration, an S/N ratio calculated with respect to a peak of light intensity distribution data serves as an index as to whether a peak value is large. Thus, it is possible to accurately determine whether a measured refractive index of a sample is acceptable using such S/N ratio.

(5) The first data acquisition processing unit may acquire light intensity distribution data along a direction parallel or perpendicular to a direction in which the slit extends in the image of the measurement light incident on the camera with respect to the image.

According to such a configuration, it is determined whether a measured refractive index of a sample is acceptable based on a peak of the light intensity distribution data along the direction parallel or perpendicular to the direction in which the slit extends in the image of the camera. For example, with regard to the peak of the light intensity distribution data along the direction parallel to the direction in which the slit extends, it is possible to determine that a measured refractive index of a sample is acceptable when the peak is not steep and a peak value is large. Meanwhile, with regard to the peak of the light intensity distribution data along the direction perpendicular to the direction in which the slit extends, it is possible to determine that a measured refractive index of a sample is acceptable when the peak is steep and a peak value is large.

(6) The refractometer may further include a notification processing unit that reports a determination result by the determination processing unit.

According to such a configuration, whether a measured refractive index of a sample is acceptable is reported as a determination result by the notification processing unit. Thus, it is possible to determine whether a value of the refractive index is reliable based on the determination result. In this way, a value of a refractive index having low reliability may be excluded from a measurement result, and thus it is possible to obtain a measurement result of a refractive index having higher reliability.

According to the invention, it is possible to accurately determine whether a measured refractive index of a sample is acceptable using not only the detected intensity of the measurement light detected by the detector but also the image of the measurement light incident on the camera. In addition, according to the invention, it is possible to automatically and easily determine whether a measured refractive index of a sample is acceptable based on each peak of light intensity distribution data, and a determination result does not vary depending on the operator.

DETAILED DESCRIPTION

Figure 1:
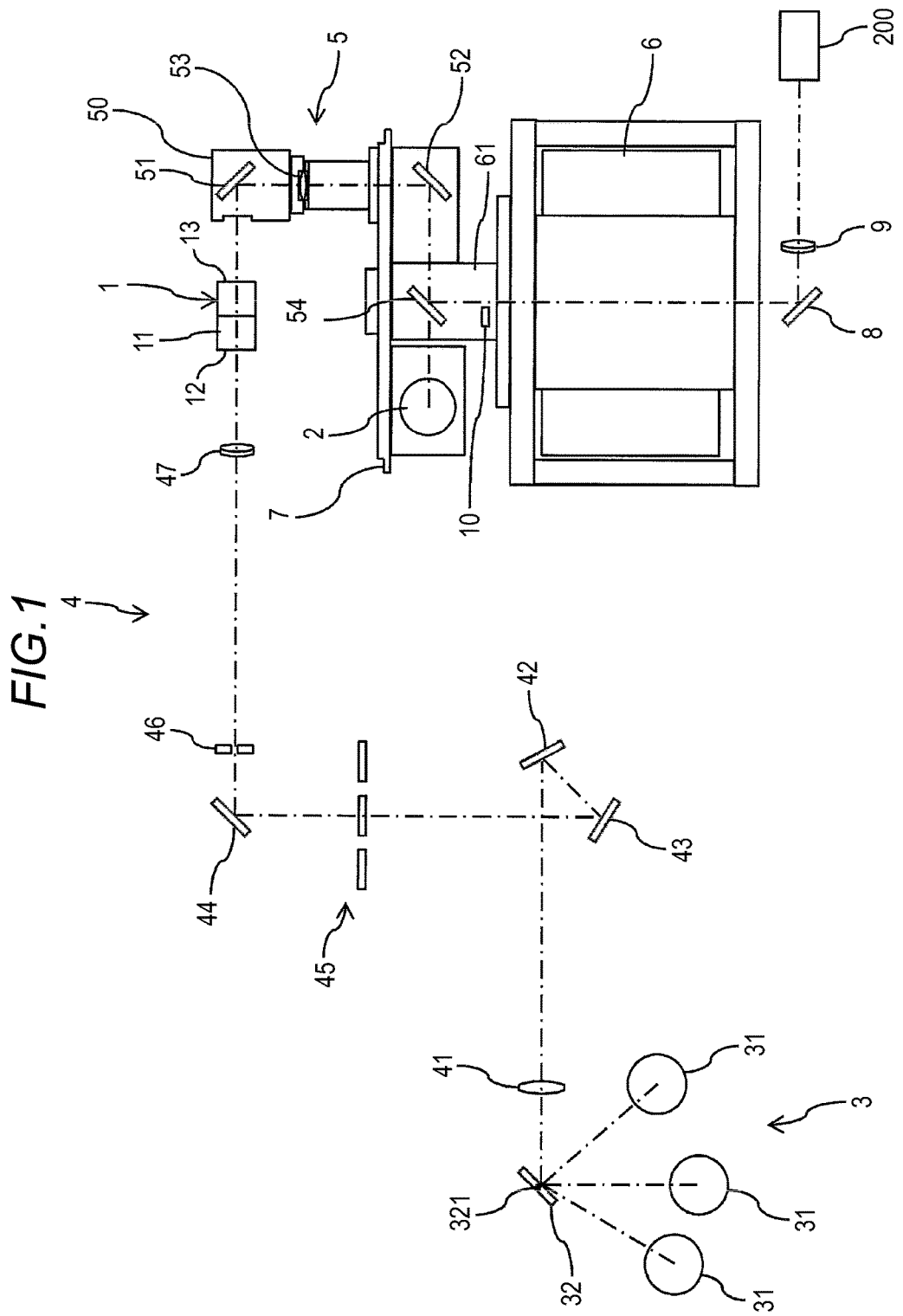
FIG. 1 is a schematic plan view illustrating a configuration example of a refractometer according to an embodiment of the invention.

FIG. 1 is a schematic plan view illustrating a configuration example of a refractometer according to an embodiment of the invention. This refractometer is a V-block refractometer that measures a refractive index of a sample by irradiating the sample with measurement light through a V-block prism 1.

Examples of the sample may include glass, plastic, liquid, etc. The sample is placed in a V-shaped groove 11 (in FIG. 1, the groove 11 is viewed from directly above) formed on the V-block prism 1, and a refractive index of the sample can be measured by detecting measurement light penetrating the sample using a detector 2.

In addition to the V-block prism 1 and the detector 2, the refractometer includes a light source unit 3 for irradiating measurement light, a first optical system 4 for guiding measurement light from the light source unit 3 to the V-block prism 1, and a second optical system 5 for guiding measurement light penetrating the V-block prism 1 to the detector 2.

The light source unit 3 includes a plurality of light sources 31. For example, a helium lamp, a hydrogen lamp, and a mercury lamp are used as the light sources 31, and measurement lights having different wavelengths such as helium d line, hydrogen C line, hydrogen F line, mercury e line, mercury g line, mercury h line, etc. may be irradiated from the light source unit 3. Measurement light from one of the light sources 31 is reflected by a mirror 32 and is irradiated in a horizontal direction from the light source unit 3. The mirror 32 is rotatable about a rotation axis 321 extending in a vertical direction (a front-back direction in a page of FIG. 1), and measurement light from the light source 31 according to a rotational position of the mirror 32 may be guided to the first optical system 4. However, the light source 31 is not limited to the above-described type.

The first optical system 4 includes a lens 41, mirrors 42, 43, and 44, an interference filter 45, a slit 46, a collimator lens 47, etc. Measurement light from the light source unit 3 passes through the lens 41, is successively reflected by the mirrors 42 and 43, and then enters the interference filter 45. A plurality of interference filters 45 is provided. When an interference filter 45 selected according to a type of the light source 31 is inserted into an optical path, only measurement light (monochromatic light) of a specific wavelength corresponding to the interference filter 45 penetrates the interference filter 45 and is guided to the mirror 44 side. Measurement light reflected by the mirror 44 passes through the slit 46, becomes parallel light by the collimator lens 47, and then enters the V-block prism 1. Measurement light incident on the V-block prism 1 from one end surface 12 passes through the sample placed in the V-shaped groove 11, then passes through the V-block prism 1 again, and is emitted from the other end surface 13 at an angle corresponding to a refractive index difference between the V-block prism 1 and the sample.

The second optical system 5 includes mirrors 51 and 52, a telemeter lens 53, a beam splitter 54, etc. The second optical system 5 is fixed to a circular plate 7 attached to a rotation shaft 61 of a motor 6. Specifically, the mirrors 51 and 52 and the telemeter lens 53 are aligned parallel to the rotation shaft 61 at a position eccentric with respect to the rotation shaft 61, and each of the mirror 52 and the beam splitter 54 is fixed to the circular plate 7 to be arranged in a direction perpendicular to the rotation shaft 61.

When the mirror 51 is disposed so that a reflecting surface thereof is inclined by 45° with respect to an incident direction of measurement light, a traveling direction of measurement light reflected by the mirror 51 is converted by 90° and guided to the telemeter lens 53. The telemeter lens 53 condenses measurement light from the V-block prism 1 and guides the condensed measurement light to the mirror 52, and measurement light reflected by the mirror 52 penetrates the beam splitter 54 and is detected by the detector 2 fixed to the circular plate 7.

The mirror 51 and the telemeter lens 53 are arranged in a line in a direction perpendicular to the incident direction of the measurement light from the V-block prism 1 and are integrally held on the circular plate 7 as a telemeter section 50 at a position eccentric with respect to the rotation shaft 61. Therefore, when the circular plate 7 is rotated around the rotation shaft 61 by rotating the motor 6, a position of the telemeter section 50 with respect to the V-block prism 1 may be changed (scanned), and the measurement light from the V-block prism 1 may be received from a different angle and guided to the detector 2. For example, the motor 6 includes a servomotor having an encoder, and a rotation angle of the motor 6 may be accurately detected.

Meanwhile, measurement light reflected by the beam splitter 54 is reflected by a mirror 8, then passes through a lens 9, and guided to a camera 200, and measurement light penetrating the sample may be captured by the camera 200. That is, measurement light passing through the slit 46 penetrates the V-block prism 1 and the sample, and then enters the camera 200. However, it is possible to adopt a configuration in which measurement light penetrating the V-block prism 1 and the sample passes through the slit 46 by disposing the slit 46 on a downstream side of the V-block prism 1. The beam splitter 54 and the mirror 8 are provided on the rotation shaft 61. When a position of the V-block prism 1 is adjusted, an autocollimation prism 10 may be inserted on an optical path between the beam splitter 54 and the mirror 8.

For example, the camera 200 may be configured by a charge coupled device (CCD) camera. The invention is not limited to a configuration in which camera 200 is provided at the above-described position. For example, it is possible to adopt a configuration in which the camera is attached to the circular plate 7 and measurement light is guided to the camera 200 through a beam splitter provided separately from the beam splitter 54, or a configuration in which two or more cameras 200 are provided.

Figure 2:
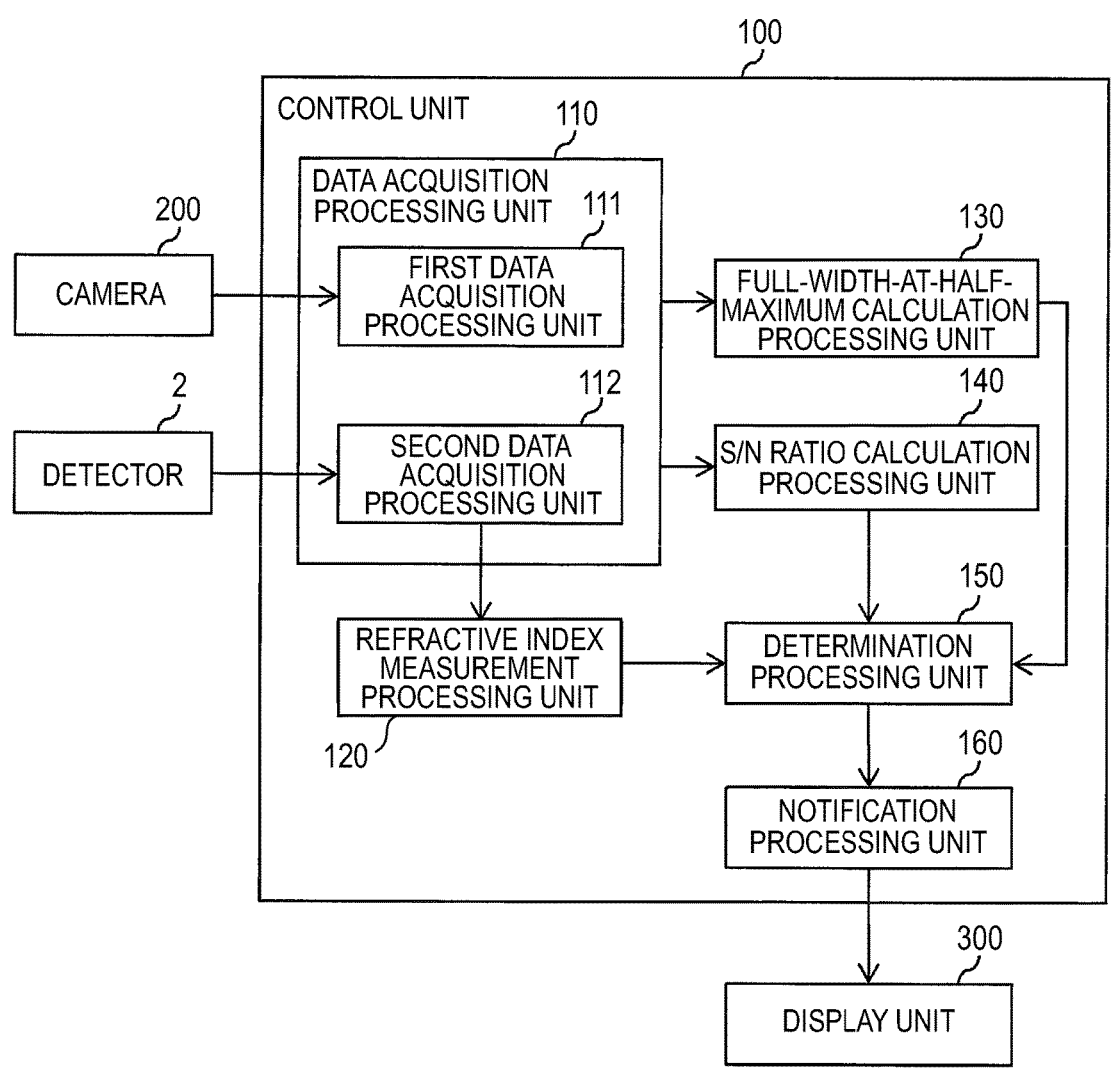
FIG. 2 is a block diagram illustrating a configuration example of a control unit in the refractometer of FIG. 1.

FIG. 2 is a block diagram illustrating a configuration example of a control unit 100 in the refractometer of FIG. 1. For example, an operation of this refractometer is controlled by the control unit 100 including a central processing unit (CPU). The control unit 100 functions as a data acquisition processing unit 110, a refractive index measurement processing unit 120, a full-width-at-half-maximum calculation processing unit 130, an S/N ratio calculation processing unit 140, a determination processing unit 150, a notification processing unit 160, etc. by the CPU executing a program.

The data acquisition processing unit 110 acquires light intensity distribution data based on an input signal from the camera 200 or the detector 2. The data acquisition processing unit 110 includes a first data acquisition processing unit 111 that acquires light intensity distribution data based on an image of measurement light incident on the camera 200 and a second data acquisition processing unit 112 that acquires light intensity distribution data based on detected intensity of measurement light detected by the detector 2.

The first data acquisition processing unit 111 acquires light intensity distribution data by processing on an image of measurement light passing through the slit 46 and entering the camera 200. The image has an elongated straight line shape corresponding to the slit 46, and a relationship between a position along a specific direction on the image and luminance (light intensity) at each position is acquired as light intensity distribution data. For example, the specific direction is a direction parallel or perpendicular to a direction in which the slit 46 extends.

The second data acquisition processing unit 112 acquires a relationship between a rotation angle of the motor 6 and detected intensity (light intensity) of the detector 2 at each rotation angle as light intensity distribution data while changing an angle at which measurement light emitted from the sample is received by rotating the motor 6. A detection signal from the detector 2 includes a noise component. However, for example, when a signal component and a noise component are separated using a well-known method such as filtering or frequency analysis, it is possible to acquire light intensity distribution data including only a signal component.

The refractive index measurement processing unit 120 measures a refractive index of the sample based on the light intensity distribution data acquired by the second data acquisition processing unit 112. Specifically, a rotation angle corresponding to highest detected intensity (peak value) is specified from detected intensities of the detector 2 at respective rotation angles of the motor 6, and the refractive index of the sample is measured based on the rotation angle and a refractive index of the V-block prism 1.

The full-width-at-half-maximum calculation processing unit (width calculation processing unit) 130 performs a process of calculating a full width at half maximum with respect to a peak of the light intensity distribution data acquired by the data acquisition processing unit 110. Specifically, in a graph of light intensity distribution data in which a vertical axis represents light intensity, a width on a horizontal axis corresponding to a half value of a peak value of the light intensity distribution data is calculated as the full width at half maximum. In the present embodiment, a description is given of a case in which a full width at half maximum is calculated with respect to each of peaks of the light intensity distribution data acquired by both the first data acquisition processing unit 111 and the second data acquisition processing unit 112. However, a full width at half maximum may be calculated with respect to only a peak of the light intensity distribution data acquired by one of the first data acquisition processing unit 111 or the second data acquisition processing unit 112. In addition, not only a width (full width at half maximum) corresponding to a range in which a ratio of light intensity to a peak value is 50% or more may be calculated, but also, for example, a width corresponding to an arbitrary ratio such as the ratio of 60% or 40% may be calculated.

The S/N ratio calculation processing unit 140 performs a process of calculating an S/N ratio with respect to the peak of the light intensity distribution data acquired by the data acquisition processing unit 110. Specifically, a ratio of a peak value (S value) in a graph of light intensity distribution data in which a vertical axis represents light intensity to amplitude (N value) of a noise component is calculated as an S/N ratio. In the present embodiment, a description is given of a case in which an S/N ratio is calculated with respect to each of the peaks of the light intensity distribution data acquired by both the first data acquisition processing unit 111 and the second data acquisition processing unit 112. However, an S/N ratio may be calculated with respect to only the peak of the light intensity distribution data acquired by one of the first data acquisition processing unit 111 or the second data acquisition processing unit 112.

The determination processing unit 150 determines whether the refractive index of the sample measured by the refractive index measurement processing unit 120 is acceptable based on each of the peaks of the light intensity distribution data acquired by the first data acquisition processing unit 111 and the second data acquisition processing unit 112. That is, it is determined whether a value of the measured refractive index of the sample is a reliable value. In the present embodiment, it is determined whether the refractive index of the sample measured by the refractive index measurement processing unit 120 is acceptable based on the full width at half maximum calculated by the full-width-at-half-maximum calculation processing unit 130 and the S/N ratio calculated by the S/N ratio calculation processing unit 140. For example, such determination of acceptability may be performed by comparing the full width at half maximum or the S/N ratio with a threshold value.

The notification processing unit 160 performs a process of reporting a determination result by the determination processing unit 150. In the present embodiment, the notification processing unit 160 displays the determination result by the determination processing unit 150 on a display unit 300 by controlling display on the display unit 300. For example, the display unit 300 may include a liquid crystal display and may be included in the refractometer or provided separately from the refractometer. The image captured by the camera 200, the light intensity distribution data acquired by the data acquisition processing unit 110, etc. are displayed on the display unit 300.

Figure 3A:
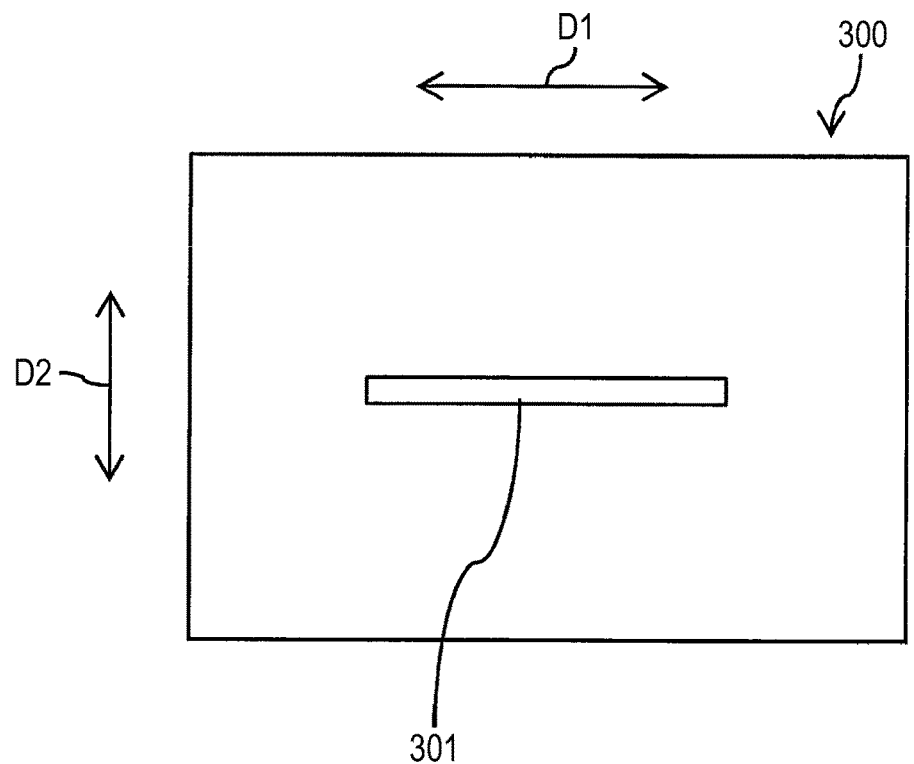
FIG. 3A is a schematic view illustrating an example of a mode in which an image captured by a camera is displayed on a display unit.
Figure 3B:
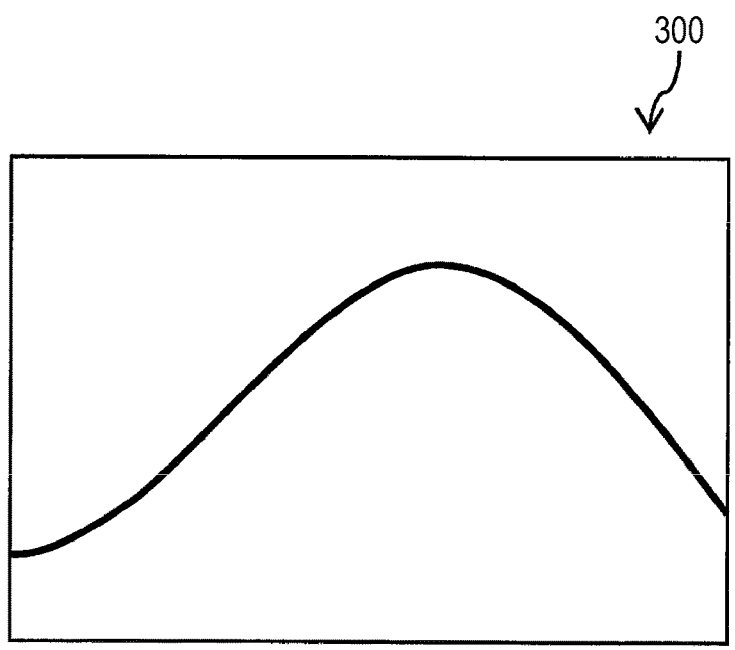
FIG. 3B is a schematic view illustrating an example of a mode in which light intensity distribution data acquired by a data acquisition processing unit is displayed on the display unit.

FIG. 3A is a schematic view illustrating an example of a mode in which the image captured by the camera 200 is displayed on the display unit 300. In addition, FIG. 3B is a schematic view illustrating an example of a mode in which the light intensity distribution data acquired by the data acquisition processing unit 110 is displayed on the display unit 300. The image captured by the camera 200 illustrated in FIG. 3A and the light intensity distribution data illustrated in FIG. 3B may be separately displayed on the display unit 300 or displayed on the same screen.

An image 301 of measurement light passing through the slit 46 is included in the image captured by the camera 200 illustrated in FIG. 3A. This image 301 has an elongated shape in a direction D1 parallel to the direction in which the slit 46 extends, and generally has a small width in a direction D2 perpendicular to the direction in which the slit 46 extends. However, the image 301 may be blurred, and thus the width in the perpendicular direction D2 may become large. In such a case, there is a possibility that the measured refractive index of the sample may not be acceptable.

The light intensity distribution data illustrated in FIG. 3B is light intensity distribution data acquired by the second data acquisition processing unit 112 and is expressed by a graph in which a horizontal axis represents the rotation angle of the motor 6 and a vertical axis represents the detected intensity (light intensity) of the detector 2. This light intensity distribution data may be displayed to change in real time as the motor 6 rotates.

Figure 4:
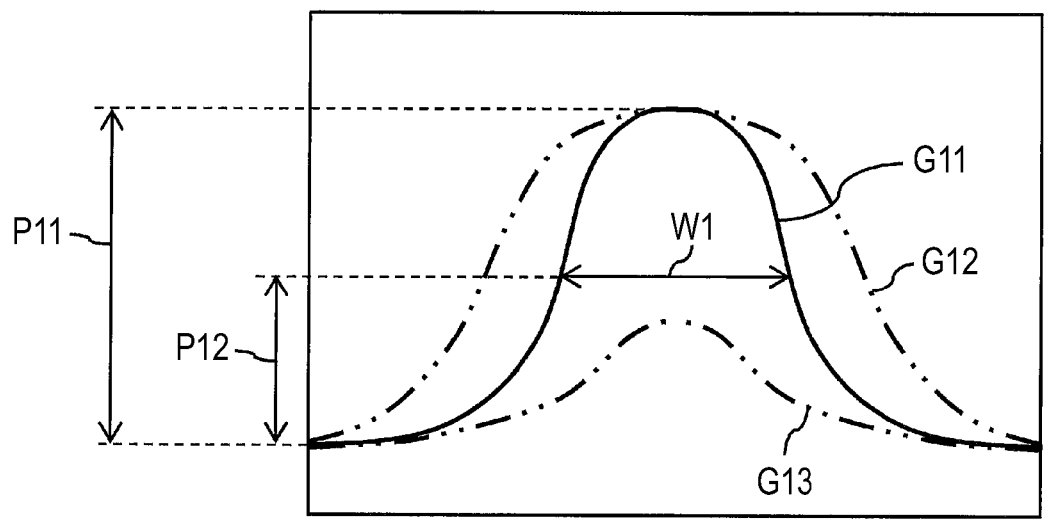
FIG. 4 is a diagram for description of a mode at the time of determining whether a measured refractive index of a sample is acceptable based on the light intensity distribution data illustrated in FIG. 3B.

FIG. 4 is a diagram for description of a mode at the time of determining whether the measured refractive index of the sample is acceptable based on the light intensity distribution data illustrated in FIG. 3B. A graph G11 illustrated in FIG. 4 is a graph in which a horizontal axis represents the rotation angle of the motor 6 and a vertical axis represents the detected intensity (light intensity) of the detector 2. A width on the horizontal axis corresponding to a value P12 which is half a peak value P11 of the graph is calculated as a full width at half maximum W1 by the full-width-at-half-maximum calculation processing unit 130.

In this case, when the full width at half maximum W1 is small and the peak is steep, the measured refractive index of the sample may be determined to be acceptable. On the other hand, when a full width at half maximum is large and a peak is not steep as illustrated by a graph G12 in FIG. 4, for example, it is possible to determine that a measured refractive index of a sample is unacceptable due to a fact that the sample having a nonuniform refractive index is measured, etc. In addition, when a peak value is small as illustrated by a graph G13 in FIG. 4, it is possible to determine that an S/N ratio is small and a measured refractive index of a sample is unacceptable.

Figure 5:
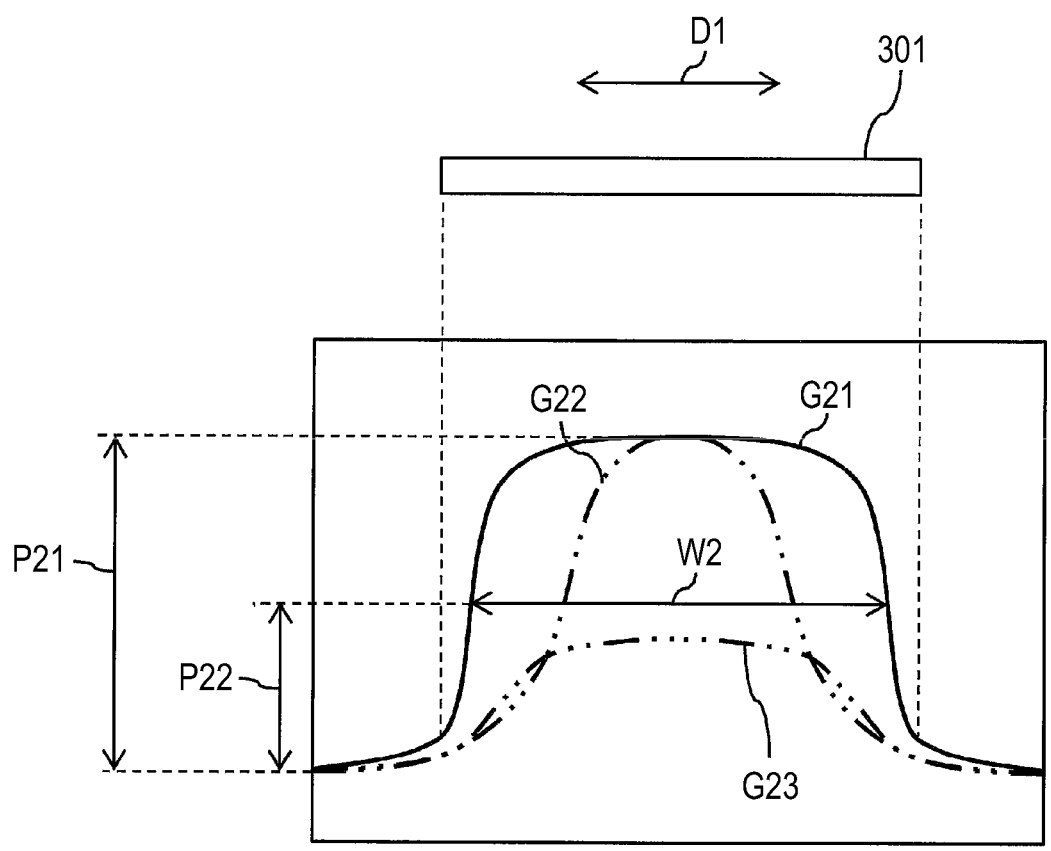
FIG. 5 is a diagram for description of a mode at the time of determining whether a measured refractive index of a sample is acceptable based on the image of the camera illustrated in FIG. 3A.

FIG. 5 is a diagram for description of a mode at the time of determining whether a measured refractive index of a sample is acceptable based on the image 301 of the camera 200 illustrated in FIG. 3A. A graph G21 illustrated in FIG. 5 is a graph in which a horizontal axis represents a position in the direction D1 parallel to the direction in which the slit 46 extends and a vertical axis represents luminance (light intensity) at each position in the image 301 of the camera 200. A width on the horizontal axis corresponding to a value P22 which is half a peak value P21 of the graph is calculated as a full width at half maximum W2 by the full-width-at-half-maximum calculation processing unit 130.

In this case, when the full width at half maximum W2 is large and the peak is not steep, luminance of the image 301 is uniform along the parallel direction D1, and it is possible to determine that the measured refractive index of the sample is acceptable. On the other hand, when a full width at half maximum is small and a peak is steep as illustrated by a graph G22 in FIG. 5, luminance of the image 301 is nonuniform along the parallel direction D1, and it is possible to determine that a measured refractive index of a sample is unacceptable. In addition, when a peak value is small as illustrated by a graph G23 in FIG. 5, an S/N ratio is small, and it is possible to determine that a measured refractive index of a sample is unacceptable.

Figure 6:
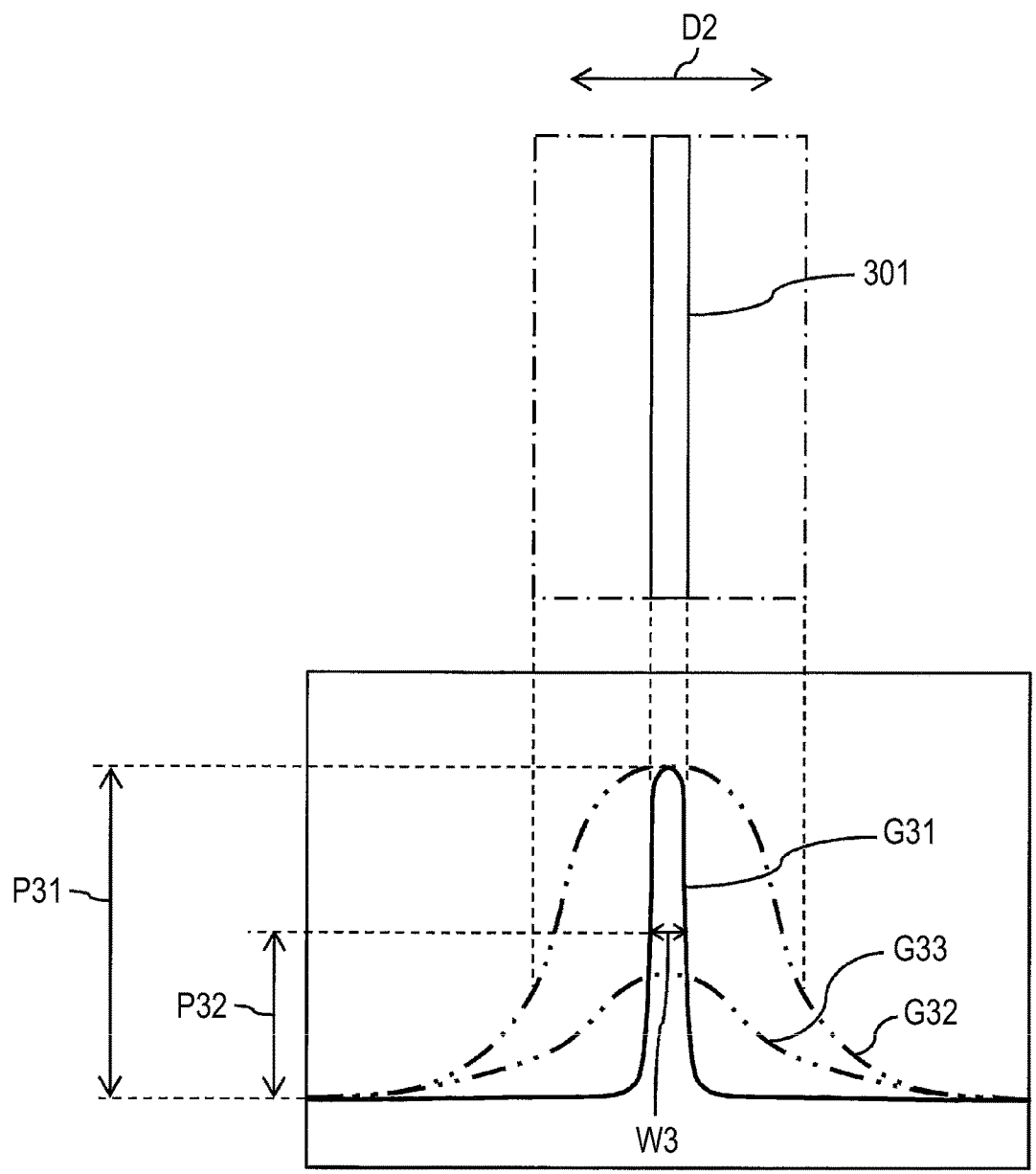
FIG. 6 is a diagram for description of another mode at the time of determining whether a measured refractive index of a sample is acceptable based on the image of the camera illustrated in FIG. 3A.

FIG. 6 is a diagram for description of another mode at the time of determining whether a measured refractive index of a sample is acceptable based on the image 301 of the camera 200 illustrated in FIG. 3A. A graph G31 illustrated in FIG. 6 is a graph in which a horizontal axis represents a position in the direction D2 perpendicular to the direction in which the slit 46 extends and a vertical axis represents luminance (light intensity) at each position in the image 301 of the camera 200. A width on the horizontal axis corresponding to a value P32 which is half a peak value P31 of the graph is calculated as a full width at half maximum W3 by the full-width-at-half-maximum calculation processing unit 130.

In this case, when the full width at half maximum W3 is small and a peak is steep, the image 301 is not blurred along the perpendicular direction D2, and it is possible to determine that a measured refractive index of a sample is acceptable. On the other hand, when a full width at half maximum is large and a peak is not steep as illustrated by a graph G32 in FIG. 6, the image 301 is blurred along the perpendicular direction D2 as indicated by a long dashed short dashed line in FIG. 6, and it is possible to determine that a measured refractive index of a sample is unacceptable. In addition, when a peak value is small as illustrated by a graph G33 in FIG. 6, an S/N ratio is small, and it is possible to determine that a measured refractive index of a sample is unacceptable.

As described above, in the present embodiment, it is determined whether a measured refractive index of a sample is acceptable based on the peak of the light intensity distribution data acquired based on the image 301 of the measurement light incident on the camera 200 (see FIG. 5 and FIG. 6) and the peak of the light intensity distribution data acquired based on the detected intensity of the measurement light detected by the detector 2 (see FIG. 4). In this way, it is possible to accurately determine whether a measured refractive index of a sample is acceptable using not only the detected intensity of the measurement light detected by the detector 2 but also the image 301 of the measurement light incident on the camera 200. In addition, it is possible to automatically and easily determine whether a measured refractive index of a sample is acceptable based on each peak of light intensity distribution data, and a determination result does not vary depending on the operator. Therefore, it is possible to easily and accurately determine whether a measured refractive index of a sample is acceptable.

In particular, the full widths at half maximums W1 to W3 calculated with respect to the peaks of the light intensity distribution data serve as indices as to whether the peaks are steep. Thus, it is possible to accurately determine whether a measured refractive index of a sample is acceptable using such full widths at half maximums W1 to W3. In addition, an S/N ratio calculated with respect to a peak of light intensity distribution data serves as an index as to whether the peak values P11, P21, and P31 are large. Thus, it is possible to accurately determine whether a measured refractive index of a sample is acceptable using such S/N ratio.

In addition, in the present embodiment, whether a measured refractive index of a sample is acceptable is reported as a determination result by the notification processing unit 160. Thus, it is possible to determine whether a value of the refractive index is reliable based on the determination result. In this way, a value of a refractive index having low reliability may be excluded from a measurement result, and thus it is possible to obtain a measurement result of a refractive index having higher reliability. The determination result reported by the notification processing unit 160 may include an alert or a warning.

In the above embodiment, a description has been given of a configuration in which the notification processing unit 160 displays the determination result by the determination processing unit 150 on the display unit 300. However, the invention is not limited to such a configuration. For example, it is possible to adopt a configuration in which the determination result by the determination processing unit 150 is reported using a method other than display such as voice.

In addition, a V-block refractometer to which the invention is applied is not limited to the configuration illustrated in FIG. 1, and various other configurations may be adopted as long as the V-block refractometer includes the detector 2, the light source unit 3, the slit 46, and the camera 200. For example, arrangement positions of the light source unit 3 and the camera 200 may be interchanged, and various mirrors and lenses may be added or omitted as appropriate.

The invention claimed is:

1. A V-block refractometer that measures a refractive index of a sample by irradiating the sample with measurement light through a V-block prism, the V-block refractometer comprising:
   a light source unit that irradiates measurement light;
   a slit through which the measurement light irradiated from the light source unit passes;
   a camera on which the measurement light passing through the slit is incident;
   a detector that detects measurement light penetrating the sample; and
   a central processing unit configured to execute a plurality of computer executable instructions in order to function as:
      a first data acquisition processing unit that acquires light intensity distribution data based on an image of the measurement light incident on the camera;
      a second data acquisition processing unit that acquires light intensity distribution data based on detected intensity of the measurement light detected by the detector;
      a refractive index measurement processing unit that measures the refractive index of the sample based on the light intensity distribution data acquired by the second data acquisition processing unit;
      a determination processing unit that determines whether the refractive index of the sample measured by the refractive index measurement processing unit is acceptable based on each of peaks of the light intensity distribution data acquired by the first data acquisition processing unit and the second data acquisition processing unit; and
      a width calculation processing unit that calculates a width corresponding to a range in which a ratio of light intensity to a peak value is a certain value or more with respect to a peak of light intensity distribution data acquired by at least one of the first data acquisition processing unit and the second data acquisition processing unit;
      wherein the determination processing unit determines whether the refractive index of the sample measured by the refractive index measurement processing unit is acceptable based on the width calculated by the width calculation processing unit.

2. The V-block refractometer according to claim 1, wherein the width corresponding to the range in which the ratio of the light intensity to the peak value is the certain value or more is a full width at half maximum.

3. The V-block refractometer according to claim 1, wherein the central processing unit is further configured to function as:
   an S/N ratio calculation processing unit that calculates an S/N ratio with respect to a peak of light intensity distribution data acquired by at least one of the first data acquisition processing unit and the second data acquisition processing unit, wherein the determination processing unit determines whether the refractive index of the sample measured by the refractive index measurement processing unit is acceptable based on the S/N ratio calculated by the S/N ratio calculation processing unit.

4. The V-block refractometer according to claim 1, wherein the first data acquisition processing unit acquires light intensity distribution data along a direction parallel or perpendicular to a direction in which the slit extends in the image of the measurement light incident on the camera with respect to the image.

5. The V-block refractometer according to claim 1, wherein the central processing unit is further configured to function as:

a notification processing unit that reports a determination result by the determination processing unit.

* * * * *